United States Patent
Kastelic et al.

(12) 
(10) Patent No.: US 6,635,671 B1
(45) Date of Patent: Oct. 21, 2003

(54) COMPOUNDS WHICH AFFECT MRNA STABILITY AND USES THEREFOR

(75) Inventors: Tania Kastelic, Coquitlam (CA); Dominique Cheneval, Coquitlam (CA); Stephan Ruetz, Riehen (CH)

(73) Assignee: Novation Pharmaceuticals Inc., British Columbia (CA)

( * ) Notice: Subject to any disclaimer, the term of this patent is extended or adjusted under 35 U.S.C. 154(b) by 0 days.

(21) Appl. No.: 09/869,078

(22) PCT Filed: Dec. 23, 1999

(86) PCT No.: PCT/CA99/01234

§ 371 (c)(1),
(2), (4) Date: Aug. 15, 2001

(87) PCT Pub. No.: WO00/38674

PCT Pub. Date: Jul. 6, 2000

(30) Foreign Application Priority Data

Dec. 24, 1998 (GB) ............................................. 9828707
Dec. 24, 1998 (GB) ............................................. 9828710

(51) Int. Cl.$^7$ ............................................. A61K 31/35

(52) U.S. Cl. ...................................... 514/450; 549/266

(58) Field of Search ........................... 549/266; 574/450

(56) References Cited

U.S. PATENT DOCUMENTS

| | | | |
|---|---|---|---|
| 4,842,862 A | 6/1989 | Jacobs et al. ................ | 424/422 |
| 5,597,846 A | 1/1997 | Sugimura et al. ............ | 514/450 |
| 5,650,430 A | 7/1997 | Sugimura et al. ............ | 514/450 |
| 5,674,892 A | 10/1997 | Giese et al. ................ | 514/450 |
| 5,728,726 A | 3/1998 | Giese et al. ................ | 514/449 |
| 5,795,910 A | 8/1998 | Giese et al. ................ | 514/450 |
| 5,977,165 A | 11/1999 | Agatsuma et al. .......... | 514/450 |

FOREIGN PATENT DOCUMENTS

| | | |
|---|---|---|
| CA | 2241624 | 5/1998 |
| CA | 2337690 | 2/2000 |
| EP | 0 460 950 A1 | 12/1991 |
| EP | 0 606 044 A1 | 7/1994 |
| GB | 9828709.7 | 12/1998 |
| WO | WO 96/25928 | 8/1996 |

OTHER PUBLICATIONS

Akashi, M. et al., "Number and Location of AUUUA Motifs: Role in Regulating Transiently Expressed RNAs," *Blood* 83:3182–3187, The American Society of Hematology (1994).

Akinaga, S. et al., "KF25706 (UCS1006–S15): A Novel derivative of radicicol inhibiting multiple: signal transduction pathways with in vivo antitumor activity in breast carcinoma xenograft models," Abstract # 2186, *Proc. Amer. Assoc. Can. Res. 39*:320, American Association for Cancer Research (Mar. 1998).

Chen, C.–Y.A. et al., "Interplay of Two Functionally and Structurally Distinct Domains of the c–fos AU–Rich Element Specifies Its mRNA–Destabilizing Function," *Mol. Cell. Biol.* 14:416–426, American Society for Microbiology (1994).

Chen, C.–Y.A. and Shyu, A.–B., "Selective Degradation of Early–Response–Gene mRNAs: Functions Analyses of Sequence Features of the AU–Rich Elements," *Mol. Cell. Biol.* 14:8471–8482, American Society for Microbiology (1994).

Chen, C.–Y.A. et al., "mRNA Decay Mediated by Two Distinct AU–Rich Elements from c–fos and Granulocyte–Macrophage Colony–Stimulating Factor Transcripts: Different Deadenylation Kinetics and Uncoupling from Translation," *Mol. Cell. Biol.* 15:5777–5788, American Society for Microbiology (1995).

Chen, C.–Y.A. and Shyu, A.–B., "AU–rich elements: characterization and importance in mRNA degradation," *TIBS* 20:465–470, Elsevier Science Ltd. (1995).

Crawford, E.K. et al., "The Role of 3' Poly(A) Tail Metabolism in Tumor Necrosis Factor–α Regulation," *J. Biol. Chem.* 272:21120–21127, The American Society for Biochemistry and Molecular Biology, Inc. (Aug. 1997).

Danner, S. et al., "Agonist Regulation of Human $\beta_2$–Adrenergic Receptor mRNA Stability Occurs via a Specific AU–rich Element," *J. Biol. Chem.* 273:3223–3229, The American Society for Biochemistry and Molecular Biology, Inc. (Feb. 1998).

Elford, P.R. et al., "A Radicicol Analogue Which Inhibits Cytokine Release In Vitro and Acute Inflammation in the Rat," *Pharmacol. Comm.* 7:301–308, Overseas Publishers Association (1996).

Feng, L. et al., "Inhibitor of Protein Tyrosine Kinase, Radicicol, Suprresses the Expression of Cyclooxygenase and Pro–Inflammatory Cytokines in LPS–Stimulated Rat Alveolar Macrophage in Part by Accelerating Degradation of mRNA," in *Eicosanoids and Other Bioactive Lipids in Cancer, Inflammation, and Radiation Injury*, Honn, K.V. et al., Eds., Kluwer Academic/Plenum Publishers, Hingham, MA, pp. 281–288 (Sep. 1997).

Kastelic, T. et al., "Induction of Rapid IL–1β mRNA Degradation in THP–1 Cells Mediated Through the AU–Rich Region in the 3'UTR by a Radicicol Analogue," *Cytokine* 8:751–761, Academic Press Limited (1996).

(List continued on next page.)

Primary Examiner—Amelia Owens
(74) Attorney, Agent, or Firm—Sterne, Kessler, Goldstein & Fox, P.L.L.C.

(57) ABSTRACT

Compounds which induce degradation of mRNA which contains one or more mRNA instability sequences are provided for use as pharmaceuticals, e.g. for use in the prophylaxis or treatment of diseases and medical conditions in general having an etiology associated with the increased or prolonged stability of mRNAs which contain one or more mRNA instability sequences, and which on prolonged or inappropriate expression typically give rise to undesirable effects, e.g. cancer cell growth or an unwanted inflammatory response.

7 Claims, 3 Drawing Sheets

OTHER PUBLICATIONS

Figure 2:
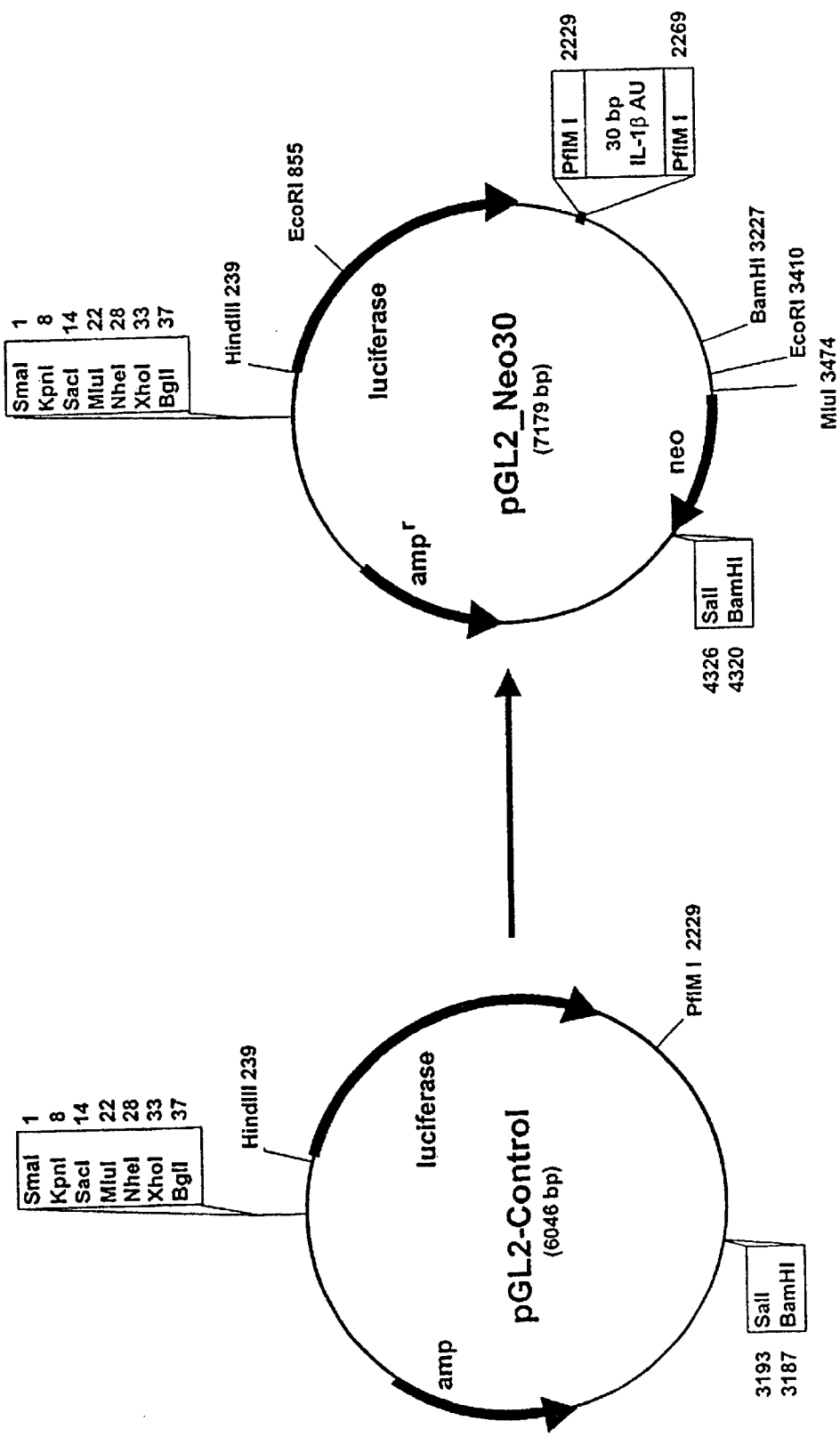

Klausner, R.D. et al., "Regulating the Fate of mRNA: The Control of Cellular Iron Metabolism," *Cell 72*:19–28, Cell Press (1993).

Lagnado, C.A. et al., "AUUUA Is Not Sufficient To Promote Poly(A) Shortening and Degradation of an mRNA: the Functional Sequence within AU–Rich Elements May Be UUAUUUA (U/A) (U/A)," *Mol. Cell. Biol. 14*:7984–7995, American Society for Microbiology (1994).

Levy, A.P. et al., "Post–transcriptional Regulation of Vascular Endothelial Growth Factor by Hypoxia," *J. Biol. Chem. 271*:2746–2753, The American Society for Biochemistry and Molecular Biology, Inc. (1996).

Lewis, T. et al., "Mapping of a Minimal AU–rich Sequence Required for Lipopolysaccharide–induced Binding of a 55–kDa Protein on Tumor Necrosis Factor–α mRNA," *J. Biol. Chem. 273*:13781–13786, The American Society for Biochemistry and Molecular Biology, Inc. (May 1998).

Nanbu, R. et al., "Multiple Instability–Regulating Sites in the 3' Untranslated Region of the Urokinase–Type Plasminogen Activator mRNA," *Mol. Cell. Biol. 14*:4920–4928, American Society for Microbiology (1994).

Sachs, A.B., "Messenger RNA Degradation in Eukaryotes," *Cell 74*:413–421, Cell Press (1993).

Shaw, G. and Kamen, R., "A Conserved AU Sequence from the 3' Untranslated Region of GM–CSF mRNA Mediates Selective mRNA Degradation," *Cell 46*:659–667, Cell Press (1986).

Shyu, A.–B. et al., "Two distinct destabilizing elements in the c–fos message trigger deadenylation as a first step in rapid mRNA decay," *Genes Dev. 5*:221–231, Cold Spring Harbor Laboratory Press (1991).

Stoecklin, G. et al., "Functional Hierarchy of AUUUA Motifs in Mediating Rapid Interleukin–3 mRNA Decay," *J. Biol. Chem. 269*:28591–28597, The American Society for Biochemistry and Molecular Biology, Inc. (1994).

Winstall, E. et al., "Rapid mRNA Degradation Mediated by the c–fos 3' AU–Rich Element and That Mediated by the Granulocyte–Macrophage Colony–Stimulating Factor 3' AU–Rich Element Occur through Similar Polysome–Associated Mechanisms," *Mol. Cell. Biol. 15*:3796–3804, American Society for Microbiology (1995).

Xu, N. et al., "Modulation of the Fate of Cytoplasmic mRNA by AU–Rich Elements: Key Sequence Features Controlling mRNA Deadenylation and Decay," *Mol. Cell. Biol. 17*:4611–4621, American Society for Microbiology (Aug. 1997).

Zhang, S. et al., "Identification and Characterization of a Sequence Motif Involved in Nonsense–Mediated mRNA Decay," *Mol. Cell. Biol. 15*:2231–2244, American Society for Microbiolgy (1995).

Zubiaga, A.M. et al., "The Nonamer UUAUUUAUU Is the Key AU–Rich Sequence Motif That Mediates mRNA Degradation," *Mol. Cell. Biol. 15*:2219–2230, American Society for Microbiology (1995).

Kastelic et al., "Assay for Identifying Compounds Which Affect Stability of mRNA," U.S. Nonprovisional Application No. 09/869,159, filed Aug. 15, 2001.

ATGGCTTCCCTAT*TTATTTATTT*ATTTGTTTGTCCAACCT
||||||||||||||||||||||||||||||||||
GGATACCGAAGGGATAAATAAATAAATAAACAAACAGGTT

FIGURE 1

COMPOUNDS WHICH AFFECT MRNA STABILITY AND USES THEREFOR

CROSS REFERENCE TO RELATED APPLICATION

This is the 371 national stage of International Application No. PCT/CA99/01234, filed Dec. 23, 1999, published in English on Jul. 6, 2000.

This invention relates to biologically active compounds and to their use in the treatment and prophylaxis of disease. In particular the invention relates to compounds which affect the stability of mRNA which contain one or more mRNA instability sequences.

Recently, it has become increasingly apparent that the regulation of RNA half-life plays a critical role in the tight control of gene expression and that mRNA degradation is a highly controlled process. RNA instability allows for rapid up- or down-regulation of mRNA transcript levels upon changes in transcription rates. A number of critical cellular factors, e.g. transcription factors such as c-myc, or gene products which are involved in the host immune response such as cytokines, are required to be present only transiently to perform their normal functions. Transient stabilisation of the mRNAs which code for these factors permits accumulation and translation of these messages to express the desired cellular factors when required; whereas, under non-stabilised, normal conditions the rapid turnover rates of these mRNAs effectively limit and "switch off" expression of the cellular factors. However, abnormal regulation of mRNA stabilisation can lead to unwanted build up of cellular factors leading to undesirable cell transformation, e.g. tumour formation, or inappropriate and tissue damaging inflammatory responses.

Although the mechanisms which control mRNA stability are far from understood, sequence regions have been identified in a number of mRNAs, which appear to confer instability on the mRNAs which contain them. These sequence regions are referred to herein as "mRNA instability sequences". For example, typical mRNA instability sequences are the AREs (AU rich elements), which are found in the 3'UTR (3' untranslated region) of certain genes including a number of immediate early genes and genes coding for inflammatory cytokines, e.g. IL-1β and TNFα.

Kastelic et al. (CYTOKINE, Vol. 8, No. 10, (October), 1996: pp751–761) have reported the finding that radicicol analog A, if added to THP-1 cells activated by IFN-Y and LPS, not only inhibited the secretion of IL-1β but also induced an extremely rapid degradation of IL-1β, IL-6 and TNF-α mRNA to undetectable levels in 5–8 h, and that this mRNA degradation appears to be mediated through AU-rich regions present in the 3' untranslated regions of the RNAs which code for these cytokines.

Previously, novel Radicicol analogs (including radicicol analog A), processes for their preparation and their pharmaceutical use were described in European patent application EP 0606044 A, together with known compounds including radicicol, O-methyl radicicol, and the related compound zearelenone and certain analogs of zearelenone. The radicicol analogs and known compounds are described in EP 0606044 A to be useful for the treatment of disorders with an etiology associated with or comprising excessive cytokine release, particularly IL-1β release, such as rheumatoid arthritis, osteoarthritis, septic shock, psoriasis, atherosclerosis, inflammatory bowel disease, Crohn's disease and asthma.

We have now found that there are other compounds in addition to radicicol analog A which induce degradation of mRNAs and that such compounds may be used for treatment of diseases and medical conditions which involve increased or prolonged stability and expression of such mRNAs. Moreover we have found that radicicol analog A may be used generally to induce degradation of mRNAs besides IL-1β, IL-6 and TNF-α mRNAs.

Accordingly the present invention provides a compound which induces degradation of mRNA which contains one or more mRNA instability sequences for use as a pharmaceutical, provided the compound is not radicicol analog A.

In a further aspect the invention provides a method for the prophylaxis or treatment of a disease or medical condition having an etiology associated with the increased stability of mRNA which contains one or more mRNA instability sequences, comprising administering to a human or animal patient an effective amount of a compound which induces degradation of the mRNA, provided that the compound is not radicicol analog A when the disease or medical condition is one with an etiology associated with or comprising excessive cytokine release, particularly IL-1β release, such as rheumatoid arthritis, osteoarthritis, septic shock, psoriasis, atherosclerosis, inflammatory bowel disease, Crohn's disease and asthma.

In a yet further aspect the invention provides use of a compound which induces degradation of mRNA which contains one or more mRNA instability sequences, for the preparation of a medicament for use in the treatment or prophylaxis of a disease or medical condition having an etiology associated with the increased stability of mRNA which contains one or more mRNA instability sequences, provided that the compound is not radicicol analog A when the disease or medical condition is one with an etiology associated with or comprising excessive cytokine release, particularly IL-1β release, such as rheumatoid arhritis, osteoarthritis, septic shock, psoriasis, atherosclerosis, inflammatory bowel disease, Crohn's disease and asthma.

The invention also provides a method for inducing degradation of mRNA in a patient, which comprises administering an effective amount of a compound which induces mRNA degradation to the patient, wherein the mRNA contains an mRNA instability sequence, provided that the compound is not radicicol analog A when the mRNA is mRNA coding for IL-1β, IL-6 or TNF-α.

Further the invention provides use of a compound which induces mRNA degradation in the preparation of a medicament for use in inducing degradation of mRNA which contains a mRNA degradation sequence in a patient, provided that the compound is not radicicol analog A when the mRNA is mRNA coding for IL-1β, IL-6 or TNF-α.

The present invention further provides the use of a radicicol analog for preparation of a medicament for treatment of a cancer and/or malignant disease.

The present invention also provides a method for the prophylaxis or treatment of a cancer and/or malignant disease comprising administering to a patient an effective amount of a radicicol analog.

Any compound which induces degradation of mRNA which contains a mRNA instability sequence is potentially of interest for use in the present invention. Compounds which induce degradation of mRNA which contains a mRNA instability sequence are hereinafter referred to as Compounds for use in the invention. Such compounds include radicicol analogs, in particular radicicol analog A or radicicol; for instance, as described in EP 0606044.

Our copending British patent application no. 9828709.7 describes a reporter gene assay for the identification of compounds which destabilise mRNA. In this assay test compounds are contacted with a DNA expression system which in the absence of the compound is capable of expressing a protein having a detectable signal, and wherein the mRNA which codes for the protein and which is transcribed from the expression system comprises at least one copy of a mRNA instability sequence. The detectable signal is measured in the presence of the test compound and the result obtained is compared with a control. Compounds which destabilise mRNAs induce degradation of the mRNA which codes for the detectable signal leading to a decrease in the magnitude of the detectable signal obtained in the reporter gene assay.

Preferred compounds for use in the present invention include compounds which may be identified as inducers of mRNA instability using the reporter gene assay as described above and as described in more detail in the above mentioned British patent application no. 9828709.7 and as hereinafter described in the Examples. Particular examples of compounds for use in the present invention include radicicol and the radicicol analogs.

Radicicol, the compound of formula I

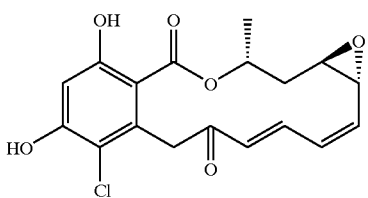

has been known for many years as a natural compound, e.g. as a metabolite of the microorganism *Monosporium bonorden*, and was described initially as having antibiotic properties (Delmotte, Nature 171, 344 (1953)).

A particular class of radicicol analogs which includes Compounds for use in the invention are compounds of formula II

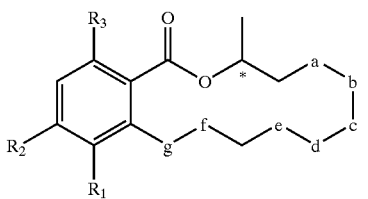

wherein
$R_1$ is H, OH, halogen, $C_1$–$C_4$ lower alkoxy, or $C_1$–$C_4$ lower alkyl-COO—;
$R_2$ is OH, $C_1$–$C_4$ lower alkoxy, or $C_1$–$C_4$ lower alkyl-COO—;
$R_3$ is H, OH, $C_1$–$C_4$ lower alkoxy, or $C_1$–$C_4$ lower alkyl-COO—;
—a—b— is —$CHR_7$—$CHR_8$— or cis or tans —$CR_7$=$CR_8$,
  wherein $R_7$ and $R_8$ are the same or different and are H, OH, $C_1$–$C_4$ lower alkoxy, or $C_1$–$C_4$ lower alkyl-COO—, or
—a—b— is —$CHR_7$—$CHR_8$— and $R_7$ and $R_8$ together with O form an epoxide bridge;
c is >CH—OH, >C=O or >$CH_2$;
—de— is —$CHR_7$—$CHR_8$— or cis or trans —$CR_7$=$CR_8$—,
  wherein $R_7$ and $R_8$ are the same or different and are H, OH, $C_1$–$C_4$ lower alkoxy, or $C_1$–$C_4$ lower alkyl-COO—, and
—f—g— is —$CH_2$—$CH_2$—, cis or trans —CH=CH—, or —C(O)—$CH_2$—, and pharmaceutically acceptable salts thereof and physiologically-hydrolysable and -acceptable esters thereof. The carbon atom marked with an asterisk (*) in formula II is an asymmetric carbon atom. The carbon atoms at a, b, c or d may also be asymmetric carbon atoms dependent upon the particular substituents present at these positions. Asymmetric carbon atoms at these positions may have the R- or S-configuration or the radicicol analog may comprise any mixture of the optical isomers thereof. Preferred isomers include those specifically described hereinafter.

Halogen or halo as used herein refers to F, Cl, Br or I unless otherwise indicated, preferably Cl.

A particular subset of the compounds of formula II are those in which one of —a—b— or —d—e— is —$CHR_7$—$CHR_8$— and the other is cis- or trans- —$CR_7$=$CR_8$—, wherein $R_7$ and $R_8$ are the same or different and are H, OH, $C_1$–$C_4$ lower alkoxy, or $C_1$–$C_4$ lower alkyl-COO—, and c is >CH—OH or >C=O, and wherein $R_1$, $R_2$, $R_3$ and —f—g— are as defined above.

Particular significances for the variable substituents and moieties of the radicicol analogs of formula II are as follows:

Preferably $R_1$ and $R_3$ are the same or different and are H, —OH, MeO— or Me—COO—. Preferably $R_2$ is —OH, MeO— or Me—COO—. More preferably $R_1$ is H or MeO; $R_2$ is MeO, and $R_3$ is OH or MeO.

Preferably —a—b— is cis- or trans- —$CR_7'$=$CR_8'$—, wherein $R_7'$ and $R_8'$ are the same or different and are H, OH, MeO— or Me—COO—. More preferably —a—b— is cis- or especially trans- —CH=CH—.

Preferably -de- is —$CHR_7'$—$CHR_8'$—, wherein $R_7'$ and $R_8'$ are as defined above. More preferably -de- is —$CH_2$—$CH_2$— or especially —CHOH—CHOH—, wherein the OH groups may be in free or protected form.

Most preferably —f—g— is trans- —CH=CH—.

Preferably the asymmetric carbon atoms of the compounds of the invention all have the S-configuration.

Particular radicicol analogs of formula II for use in the invention are analogs of formula II in which $R_1$ is H or methoxy, $R_2$ is methoxy, $R_3$ is OH, —a—b— is cis- or trans-—CH=CH—, c is CHOH or C=O, —d—e— is —CHOH—CHOH— and —f—g— is trans- —CH=CH—; in free form or base salt form or in the form of a physiologically-hydrolysable and -acceptable ester.

Particular radicicol analogs for use in the present invention include radicicol and O-lower alkyl radicicols, i.e. the compounds of formula I'

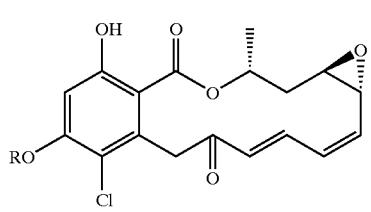

where R is H or $C_1$–$C_4$ lower alkyl, e.g. methyl, and pharmaceutically acceptable salts thereof and physiologically-hydrolysable and -acceptable esters thereof.

For the purposes of the present description a radicicol analog is a compound having the characteristic bicyclic ring structure of radicicol, i.e. the structure of formula I",

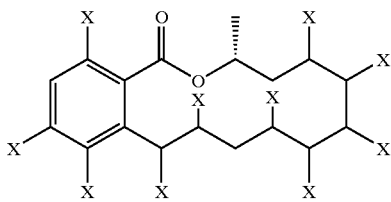

I"

wherein the X groups are separately H or substituents, the 14-membered lactam ring may additionally comprise one or more, e.g. two, ethylenically unsaturated bonds and at least one of the X substituents of the lactam ring may comprise an oxy (=O), or (with an adjacent X substituent) an epoxide substituent, and pharmaceutically acceptable salts thereof and physiologically-hydrolysable and -acceptable esters thereof.

Radicicol analogs which comprise —OH substituents may also exist in the form of pharmaceutically acceptable esters, and the use of such is included within the scope of the invention. Pharmaceutically acceptable esters are preferably prodrug ester derivatives, such being convertible by solvolysis or under physiological conditions to the free radicicol analog. Preferred pharmaceutically acceptable prodrug esters of the are those derived from a carboxylic acid, a carbonic acid monoester or a carbamic acid, advantageously esters derived from an optionally substituted lower alkanoic acid or an arylcarboxylic acid.

Radicicol analogs may also exist in the form of pharmaceutically acceptable salts, and the use of such is included within the scope of the invention. Pharmaceutically acceptable salts represent acid addition salts with conventional acids, for example, mineral acids, e.g., hydrochloric acid, sulfuric or phosphoric acid, or organic acids, for example, aliphatic or aromatic carboxylic or sulfonic acids, e.g., acetic, propionic, succinic, glycolic, lactic, malic, tartaric, citric, ascorbic, maleic, fumaric, hydroxymaleic, pyruvic, pamoic, methanesulfonic, toluenesulfonic, naphthalenesulfonic, sulfanilic or cyclohexylsulfamic acid; also amino acids, such as arginine and lysine. For compounds of the invention having acidic groups, for example, ian acidic —OH group, pharmaceutically acceptable salts also represent metal or ammonium salts, such as alkali metal or alkaline earth metal salts, e.g., sodium, potassium, magnesium or calcium, salts.

EP 0606044 A describes the isolation and characterisation of the radicicol analog of formula III,

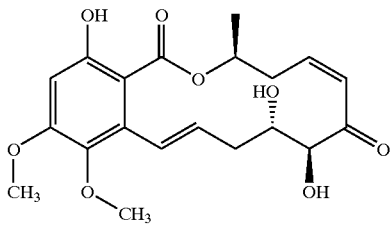

III hereinafter referred to as radicicol analog A, which was first identified as a natural product isolated from a strain of pycnidia imperfect fungi (F/87-250904) deposited on Nov. 6, 1991 with the ARS Patent Culture Collection, US Dept. of Agriculture, Northern Regional Research Centre, Peoria, Ill., USA under the provisions of the Budapest Treaty as deposit NRRL 18919.

Radicicol analog A is a particularly preferred radicicol analog for use in the present invention. Radicicol analog A also serves as a valuable starting material for synthesis of other radicicol analogs for use in the present invention. Alternatively EP 0606044 A describes the de novo synthesis of radicicol analogs starting from readily available starting materials.

Novel Radicicol analogs, processes for their preparation and their pharmaceutical use are described in European patent application EP 0606044 A, together with known compounds including radicicol, O-methyl radicicol, and the related compound zearelenone and certain analogs of zearelenone. The radicicol analogs and known compounds are described in EP 0606044 A to be useful for the treatment of disorders with an aetiology associated with or comprising excessive cytokine release, particularly IL-1β release, such as rheumatoid arthritis, osteoarthritis, septic shock, psoriasis, atherosclerosis, inflammatory bowel disease, Crohn's disease and asthma.

The disclosure of EP 0606044 relating to the isolation of radicicol analog A from the fungal strain F/87-250904, the synthesis of semi-synthetic radicicol analogs from radicicol analog A and the de novo synthesis of radicicol analogs, is specifically incorporated by reference in the teaching of the present application.

Surprisingly it has now been found that radicicol, radicicol analogs, zearelenone and zearelenone analogs (hereinafter collectively referred to as radicicol analogues), such as those described in EP 0606044 A, are useful for treatment of certain forms of cancer and malignant diseases.

Particularly preferred radicicol analogs for use in the invention include compounds of formula II in which —a—b— is trans- —CH=CH—, e.g. the compounds of formulae IV, V and VI

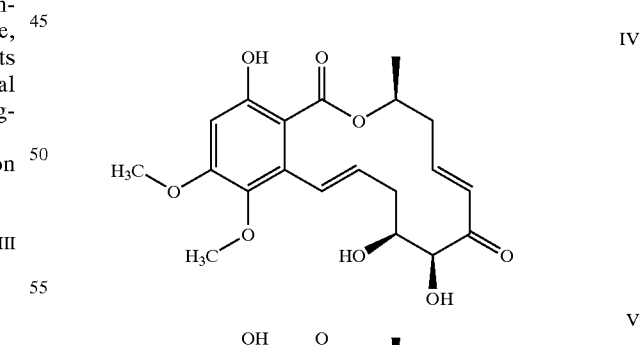

IV

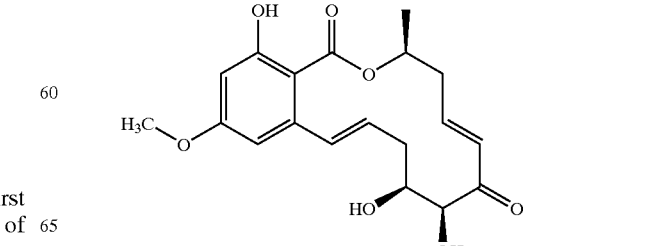

V

VI

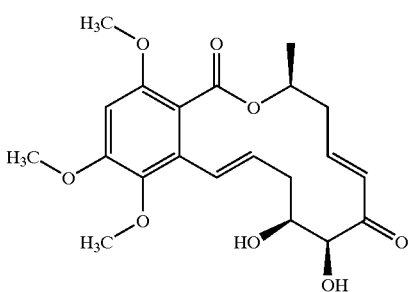

Particularly preferred radicicol analogs for use in the invention include compounds of formula II in which —a—b— is trans- —CH=CH—, e.g. the compounds of formulae III, VII and VIII.

III

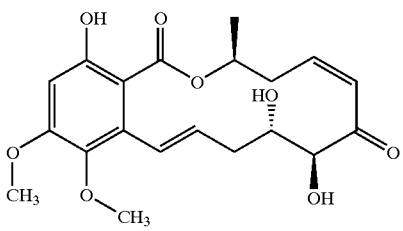

VII

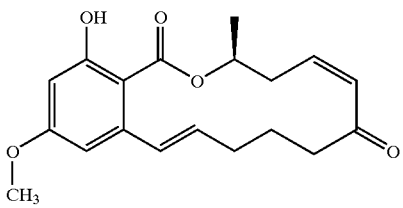

VIII

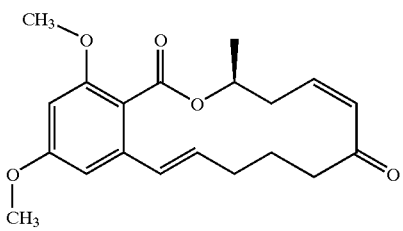

The present invention may be used in the prophylaxis or treatment of diseases and medical conditions in general having an etiology associated with the increased or prolonged stability of mRNAs which contain one or more mRNA instability sequences, and which on prolonged or inappropriate expression typically give rise to undesirable effects, e.g. cancer cell growth or an unwanted inflammatory response.

mRNA instability sequences have been identified in the UTRs, in particular the 3'UTRs, of a large number of transiently expressed genes including genes for cytokines, chemokines, nuclear trascription factors, protooncogenes, immediate early genes, cell cycle controlling genes, oxygenases, and genes involved in and controlling of apoptosis. The natural RNA sequences which comprise the mRNA instability sequences are alternatively referred to as adenylate/uridylate (AU)-rich elements, or AREs. Transiently expressed genes which contain mRNA instability sequences include, for example, the genes coding for GM-CSF, c-fos, c-myc, c-jun, krox-20, nur-77, zij268, β-IFN, uPA, IL-1, IL-3, TNF-α, MCP1, synl, $β_2$-AR, E-selectin, VCAM-1, ICAM-1, P-glycoproteins (MDR), MRPs, Pγhl (pf mdr), COX II, metalloproteinases (MMPs), bcl-2 and MIP-2 α.

The following publications include extensive discussion of mRNA instability sequences and AREs, the sequences motifs which they contain and (minimum) sequence requirements for mRNA destabilisation, as well as identifying a number of mRNA instability sequences and the genes which contain them:

Shaw & Kamen, Cell, Vol. 46, 659–667, Aug. 29, 1986 (GM-CSF);
Shyu et al., Genes & Development, 5:221–231 (1991) (c-fos);
Sachs, Cell, Vol. 74, 413–421, Aug. 13, 1993 (Review. "Messenger RNA Degradation in Eukaryotes");
Chen et al., Mol. Cell. Biol., January 1994, p416–426 (cfos);
Akashi et al., Blood, Vol. 83, No. 11, (Jun. 1), 1994: pp 3182–3187 (GM-CSF etc.);
Nanbu et al., Mol. Cell. Biol., July 1994, p. 4920–4920 (Upa);
Stoecklin et al., J. Biol. Chem., Vol. 269, No. 46, Nov.18, 1994, pp 28591–28597 (IL-3);
Lagnado et al., Mol. Cell. Biol., December 1994, p. 7984–7995 (general);
Zhang et al., Mol. Cell. Biol., April 1995, p. 2231–2244 (yeast);
Zubiaga et al., Mol. Cell. Biol., April 1995, p. 2219–2230 (general);
Winstall et al., Mol. Cell. Biol., July 1995, p. 3796–3804 (c-fos, GM-CSF);
Chen et al., Mol. Cell. Biol., October 1995, p. 5777–5788 (c-fos, GM-CSF);
Chen et al., TIBS Nov. 20, 1995, 465–470 (review);
Levy et al., J. Biol. Chem., Vol. 271, No. %, Feb. 2, 1996, pp. 2746–2753 (VEGF);
Kastelic et al., Cytokine, Vol. 8, No. 10 (October), 1996: pp751–761;
Crawford et al., J. Biol. Chem., Vol. 272, No. 34, Aug.22, 1997, pp. 21120–21127 (TNFα);
Xu et al., Mol. Cell. Biol., August 1997, Vol. 18, No. 8, p. 4611–4621 (general);
Danner et al., J. Biol. Chem., Vol.273, No. 6, Feb.6, 1998, pp. 3223–3229 (human $β_2$-Adrenergic Receptor);
Lewis et al., J. Biol. Chem., Vol. 273, No. 22, May 29 1998, pp. 13781–13786 (TNF-α).

As described in the above publications mRNA instability sequences often contain one or more copies of sequence motifs, e.g. selected from: AUUUA, UAUUUAU, UUAUUUA(U/A)(U/A), and AUUUAUUUA. Such sequence motifs are typically in genes between the stop codon and the poly A signal and may associated with appropriate flanking sequences and may interact in combination with other sequences, e.g. present in the 5' UTR and e.g. with instability motifs present in the coding region.

The present invention may be used in connection with diseases and medical conditions associated with any of the genes mentioned above or described in the listed publications, which comprise mRNA instability sequences.

Examples of diseases and medical conditions which may be treated or prevented by use of the present invention include: cancers e.g. of the colon, breast, lung etc., acute and chronic inflammation, autoimmune diseases, respiratory diseases, infectious diseases and transplant rejection.

The compounds for use in the invention have valuable pharmacological properties. In particular compounds for use in the invention have valuable properties as inducers of degradation of mRNAs which contain mRNA instability sequences. The activity of compounds for use in the invention as inducers of mRNA degradation may be demonstrated by means of a reporter gene assay as hereinafter described in the Examples, or as described in more detail in our copending British patent application no. 9828709.7.

In view of their activity as inducers of degradation of mRNAs which contain mRNA instability sequences, the radicicol analogues are useful for the prophylaxis and treatment of cancers and malignant diseases which involve inappropriate build-up and expression of mRNAs, which contain mRNA instability sequences, and which code for proteins involved in the initiation, progression or persistence of cancer or malignant disease. Examples of cancer related genes, with mRNAs which contain mRNA destabilising sequences, include various oncogenes and transcription factors, e.g. c-myc, c-fos, Sp1, bcl-2 and similar genes. The inappropriate or prolonged expression of such oncogenes is implicated in the initiation of certain forms of cancer, such as colon cancer, breast cancer, lung cancer etc.. Further examples of cancer related genes, with mRNAs which contain mRNA instability sequences are genes for metalloproteinase enzymes, e.g. MMP-1, MMP-2, collagenases etc., involved in tissue remodelling required for tumour growth and metastasis invasion; cell cycle related genes such as p45/SKIP2 etc. and multidrug resistance genes, e.g. mdr-1, MRPs, etc. involved in the intrinsic or acquired multidrug resistance of some cancer cells.

Treatment with radicicol analogs advantageously leads to degradation of the m1RNAs of such genes, resulting in the down-regulation or "switching off" of gene expression. Thus for example, radicicol analogs may be use for treatment and prevention of oncogene mediated cancers and malignant diseases, to treat or prevent tumour growth and metastasis invasion in general, and to prevent or reverse multidrug resistance and thereby facilitate cancer and tumour treatment with conventional, e.g. cytotoxic, anti-cancer agents.

Radicicol analogs may be tested for their activity as anticancer agents in cell or in vivo assays substantially as described below or in variants of such assays using appropriate cell lines and conditions.

Radicicol analogs exhibit, for example, inhibition of the cell growth of EGF-dependent cell lines, for example the epidermoid BALB/c mouse keratinocyte cell line (see Weissmann, B. A., and Aaronson, S. A., Cell 32 599 (1983)) or the A431 cell line, which are recognised useful standard sources of EGF-dependent epithelial cells (see Carpenter, G., and Zendegni, J. Anal. Biochem. 153, 279–282 (1985)). In a known test method (see Meyer et al., Int. J. Cancer 43, 851 (1989)), the inhibitory activity of radicicol analogs is determined, briefly, as follows: BALB/MK cells (10 000/microtitre plate well) are transferred to 96 well microtitre plates. The test compounds (dissolved in DMSO) are added in a series of concentrations (dilution series) in such a manner that the final concentration of DMSO is not greater than 1% (v/v). After the addition, the plates are incubated for three days during which the control cultures without test compound are able to undergo at least three cell-division cycles. The growth of the MK cells is measured by means of methylene blue staining: after the incubation the cells are fixed with glutaraldehyde, washed with water and stained with 0.05% methylene blue. After a washing step the stain is eluted with 3% HCl and the optical density per well of the microtitre plate is measured using a Titertek multiskan at 665 nm. $IC_{50}$ values are determined by a computer-aided system using the formula:

$$IC_{50}=[(OD_{test}-OD_{start})/(OD_{control}-OD_{start})]\times 100.$$

The $IC_{50}$ value in those experiments is given as that concentration of the test compound in question that results in a cell count that is 50% lower than that obtained using the control without inhibitor. The radicicol analogs exhibit inhibitory activity in the micromolar range, for example an $IC_{50}$ of approximately from 0.1 to 10 mM, especially from 0.4 to 4 mM.

The radicicol analogs exhibit inhibition of the growth of tumour cells also in vivo, as shown, for example, by the test described below: the test is based on inhibition of the growth of the human epidermoid carcinoma A43 1 (ATCC No. CRL 1555; American Type Culture Collection, Rockville, Md., USA; see Santon, J. B., et al., Cancer Research 46 4701–4705 (1986) and Ozawa, S., et aL, Int. J. Cancer 40, 706–710 (1987)), which is transplanted into female BALB/c nude mice (Bomholtgard, Denmark). That carcinoma exhibits a growth that correlates with the extent of the expression of EGF-receptor. In the experiment, tumours having a volume of approximately 1 $cm^3$ cultured in vivo are surgically removed from experimental animals under sterile conditions. The tumours are comminuted and suspended in 10 volumes (w/v) of phosphate-buffered saline. The suspension is injected s.c. (0.2 ml/mouse in phosphate-buffered saline) into the left flank of the animals. Alternatively, $1\times 10^6$ cells from an in vitro culture can be injected in 0.2 ml of phosphate-buffered saline. Treatment with test compounds is started 5 or 7 days after the transplant, when the tumours have reached a diameter of 4–5 mm. The test compound in question is administered (in different doses for different animal groups) once a day for 15 successive days. The tumour growth is determined by measuring the diameter of the tumours along three axes that are perpendicular to each other. The tumour volumes are calculated using the known formula $p\times L\times D^2/6$ (see Evans, B. D., et al., Brit. J. Cancer 45, 466–468 (1982)). The results are given as treatment/control percentages (TIC×100=T/C%). At a dose of from 3 to 50 mg/kg active ingredient, distinct inhibition of the tumour growth is found, for example T/C% values of less than 10, which indicates strong inhibition of tumour growth.

The radicicol analogs for use in the invention can be used both alone and in combination with other pharmacologically active compounds, for example together with inhibitors of the enzymes of polyamine synthesis, inhibitors of protein kinase C, inhibitors of other tyrosine kinases, cytokines, negative growth regulators, for example TGF-β or IFN-β, aromatase inhibitors, antioestrogens and/or cytostatic agents.

Characteristically when the radicicol analogs are use to prevent or reverse multidrug resistance of tumour and other malignant cells, they are used in combination with cytostatic or cytotoxic agents. A suitable cell-based assay for assessing utility in restoring sensitivity of cancer cells to antineoplastic/cytotoxic, drug substances in vitro is as follows.

Cancer cell lines (CCL), e.g. from human small cell carcinoma of the lung, resistant to one or more cancer therapeutic drug substances (CTDS) selected from the group comprising Daunorubicin (DR); Vincristine (VC); Adriamycin (AM); Etoposide (ET); Tenoposide (TE); Colchicine (CC); and Taxol are developed in accordance with the methods described by Twentyman et al., Br. J. Cancer, 54, 253 (1986).

Sensitivity of resistant sub-lines (CCL-R) is compared with parental sensitive lines (CCL-S)by assaying inhibition of cell growth during continuous CTDS exposure, e.g. in the case of a DR-resistant line (CCL-DRR)by comparing growth of CCL-DRS and CCL-DRR lines in the presence of DR contained in the growth medium ab initio. For the purpose, cell proliferation is measured by cell counting using an electronic cell counter, counting being effected close to the termination of the exponential growth phase. CCL-R lines are selected for which the $IC_{50}$ (drug concentration, e.g. DR concentration, required to reduce final cell number to 20% of that for non-CTDS (e.g. DR) treated controls is >80×, preferably >100×, greater than that of the parental CCL-S lines.

Sensitivity of selected CCL-R lines to CTDS (e.g. DR) in the presence or absence of test radicicol analog is then performed, employing cell counting as a measure of proliferation as described above. For this purpose cells are cultured ab initio in the presence of varying concentrations of both CTDS and test radicicol analog. For screening, concentrations of the latter are chosen which do not themselves cause a significant reduction in proliferation. Appropriate concentrations are established by culturing CCL-S and CCL-R in the presence of varying concentrations of radicicol analog in the absence of CTDS. Radicicol analogs are routinely tested at concentrations of from 0.01 to 50, in particular 0.1 to 10 µg/ml, e.g. at concentrations of 0.01, 0.02, 0.05, 0.1, 0.2, 0.5, 1.0, 2.0, 5.0, 10.0 and 50 µg/ml. The ratio of CTDS (e.g. DR) required to inhibit cell proliferation by 50% in the absence of test radicicol analog ($IC_{50}$–CS) compared with that obtained in the presence of test radicicol analog ($IC_5$+CS) is taken as a measure of increased sensitivity of the CCL-R line to CTDS which has been induced by the radicicol analog. Stability of the CCL-R line used is ensured by cross checking its sensitivity to CTDS with that previously established.

Additional procedures for assessing utility in restoring sensitivity of cancer cells to anti-neoplastic/cytotoxic, drug substances, including in vivo procedures are described in EP 0296122 B, the relevant disclosures of which are incorporated by reference in the teaching of the present application.

Compounds for use in the Invention can be used both alone and in combination with other pharmacologically active compounds, for example in cancer treatment the compounds may be used together with inhibitors of the enzymes of polyamine synthesis, inhibitors of protein kinase C, inhibitors of other tyrosine kinases, cytokines, negative growth regulators, for example TGF-β or IFN-β, aromatase inhibitors, antioestrogens and/or cytostatic agents.

Suitable pharmaceutical compositions comprising Compounds for use in the invention as active ingredient and that can be used especially in the treatment of the diseases mentioned above include compositions for enteral, such as nasal, buccal, rectal or especially oral, administration and parenteral, such as intravenous, intramuscular or subcutaneous, administration to warm-blooded animals, especially human beings. The compositions comprise the active ingredient on its own or preferably together with a pharmaceutically acceptable carrier. The dosage of the active ingredient depends on the disease to be treated, and on species, age, weight and individual condition, individual pharmacokinetic conditions, and the mode of administration.

The pharmaceutical compositions may comprise from approximately 1% to approximately 95% active ingredient, forms of administration in single dose form preferably comprising from approximately 20% to approximately 90% active ingredient and forms of administration that are not in single dose form preferably comprising from approximately 5% to approximately 20% active ingredient. Unit dose forms are, for example, dragées, tablets, ampoules, vials, suppositories or capsules. Other forms of administration are, for example, ointments, creams, pastes, foams, tinctures, lipsticks, drops, sprays, dispersions, etc. Examples are capsules comprising from approximately 0.05 g to approximately 1.0 g of the active ingredient.

The pharmaceutical compositions are prepared in a manner known per se, for example by means of conventional mixing, granulating, confectioning, dissolving or lyophilising procedures.

Solutions of the active ingredient, and also suspensions or dispersions, especially isotonic aqueous solutions, dispersions or suspensions, are preferably used, it being possible, for example in the case of lyophilised compositions that contain the active ingredient alone or together with a carrier, for example mannitol, for such solutions, suspensions or dispersions to be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers, and are prepared in a manner known per se, for example by means of conventional dissolving or lyophilising procedures. The said solutions or suspensions may comprise viscosity-increasing substances, such as sodium carboxymethyl-cellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid, or corresponding unsaturated acids, for example oleic acid, elaidic acid, erucic acid, brassidic acid or linoleic acid, if desired with the addition of antioxidants, for example vitamin E, β-carotene or 3,5di-tert-butyl4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossd, Paris), "Labrafil M 1944 CS" (unsaturated polyglycolised glycerides prepared by alcoholysis of apricot kernel oil and consisting of glycerides and polyethylene glycol ester, Gattefossé, France), "Labrasol" (saturated polyglycolised glycerides prepared by alcoholysis of TCM and consisting of glycerides and polyethylene glycol ester, Gattefosse, France) and/or "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into, for example, ampoules or vials and to sealing the containers.

Pharmaceutical compositions for oral administration can be obtained, for example, by combining the active ingredient with one or more solid carriers, if desired granulating a resulting mixture, and processing the mixture or granules, if desired, and if necessary by the addition of additional excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, or alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethylcellulose phthalate. Colourings or pigments may be added to the tablets or dragee coatings, for example for identification purposes or to indicate different doses of active ingredient.

Orally administrable pharmaceutical compositions also include dry-filled capsules consisting of gelatin, and also soft, sealed capsules consisting of gelatin and a plasticiser, such as glycerol or sorbitol. The dry-filled capsules may contain the active ingredient in the form of granules, for example in admixture with fillers, such as corn starch, binders and/or glidants, such as talc or magnesium stearate, and optionally stabilisers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilisers and detergents, for example of the polyoxyethylene sorbitan fatty acid ester type, may also be added.

Other oral forms of administration are, for example, syrups prepared in customary manner which comprise the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single dose quantities.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration there are suitable especially aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilisers. The active ingredient, optionally together with excipients, can also be in the form of a lyophilisate and can be made into a solution prior to parenteral administration by the addition of suitable solvents.

The Compounds for use in the invention can be administered, prophylactically or therapeutically, as such or in the form of pharmaceutical compositions, preferably in an amount effective against the said diseases, to a warm-blooded animal, for example a human being, requiring such treatment, the compounds being used especially in the form of pharmaceutical compositions. In such treatment an individual of about 70 kg body weight will be administered a daily dose of from approximately 0.1 g to approximately 5 g, preferably from approximately 0.5 g to approximately 2 g, of a compound of formula II.

The following Examples serve to illustrate the invention and refer to the accompanying Figures, in which FIG. 1 which shows the 30 bp fragment used as a mRNA instability sequence in the porter gene assay of Example 1 (SEQ ID NOS: 1 and 2);

FIG. 2 which shows plasmid diagrams for pGL2_Neo30 and pGL2-Control; and

Figure 3:
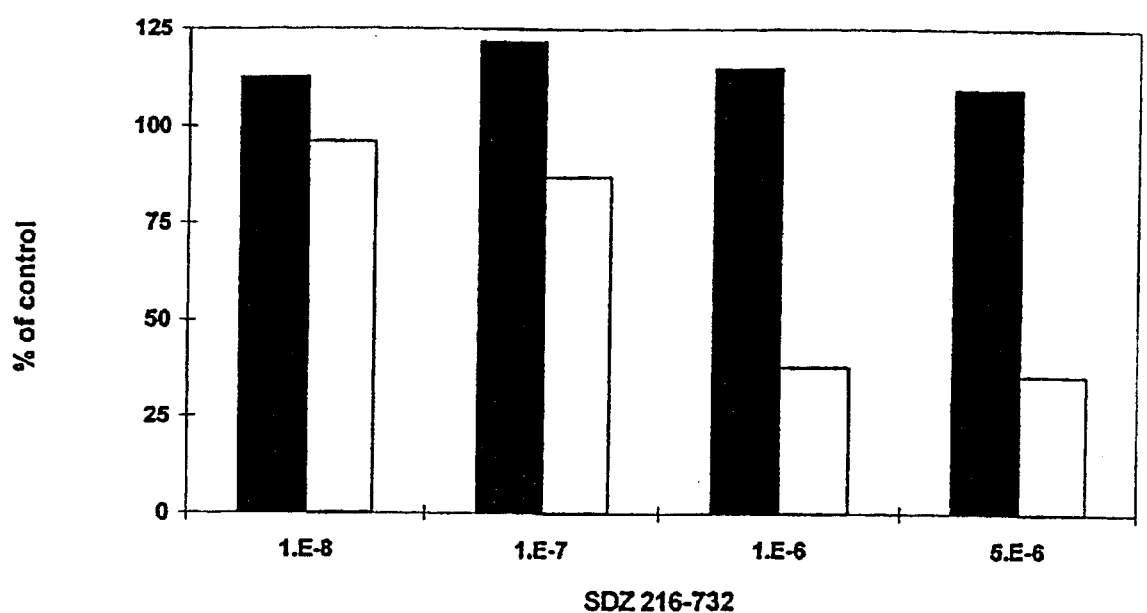

FIG. 3 shows graphs of luciferase activity from clones 53 (solid bars) and 63 (open bars) treated with various concentrations of radicicol analog A (SDZ 216-732).

EXAMPLES

Example 1

Reporter Gene Assay for Compounds Which Destabilise mRNA

A. Construction of pGL2 neo30

In order to obtain a vector for stable integration into THP-1 cells, a XhoI-SalI fragment of the neo resistant gene (expressing aminoglycoside 3' phosphotransferase) derived from pMCIneo (Stratagene) is subcloned into the SalI site of pGL2Control (Promega). This resulting plasmid was called pGL2_Neo. A 30 bp fragment (containing three tandem AUUUA motifs, based on the IL-Iβ3'UTR sequence) obtained by annealing two complementary synthetic oligonucleotides (see FIG. 1) is subcloned into pGL2 Neo using the PflM1 restriction site. This results in the luciferase expression vector pGL2_Neo30 (FIG. 2). FIG. 1 shows the IL-1β3'UTR sequence containing three tandem AUUUA motifs used for ligation into the PflMI site of pGL2_Neo.

B. Transfection and Selection of Stable Cell Lines

The resulting vectors pGL2_Neo30 and pGL2_Neo are transfected into THP-1 cells by electroporation. $10^7$ cells/ml in 1.3 mM $KH_2PO_4$, 7.36 m.M $Na_2HPO_4$, 2.44 mM KCl, 124 mm NaCl, 5 mM glucose, 9.6 μM $MgCl_2$ and 16 μM $CaCl_2$ pH 7.2 are transfected with 20 μg of DNA in a Bio-Rad Gene Pulser (250V, 690 μF and indefinite resistance) using a 0.4 cm cuvette. Cells are subsequently cultured in RPMI medium containing 10%FBS, 2mM L-Gln (L-glutamine), 50 μM 2mercaptoethanol and 600 μg/ml of G418 (geneticin). After transfection of pGL2_Neo30 and pGL2_Neo into THP-1 cells, stable cell lines are obtained by selection for G418 resistance and assayed for luciferase activity. One cell line of each transfection is chosen for further analysis; the pGL2_Neo30 cell line is referred to as clone No. 63 and the pGL2_Neo cell line as clone No. 53. No endogenous luciferase activity could be detected in normal THP-1 cells.

The tissue culture and luciferase activity measurements are carried out as described below.

C. Tissue Culture

The transfected human monocytic leukemia cell lines, clones No. 53 and 63 are grown in RPMI medium supplemented with 110 U/ml penicillin, 100 μg/ml streptomycin, 2 mM L-Gln and 2 g/l $NaHCO_3$. Heat-treated FBS (5%) is added before use. The cells are grown to a density of $5 \times 10^5$/ml and induced to differentiate with 100 U/ml (final concentration) γIFN. Three hours later, 10 μl of LPS (5 μg/ml final concentration) is added. This time point is designated time 0. Compounds are added at various times after LPS addition as indicated.

D. Luciferase Activity Measurement

In order to adapt the system to the use of 96 well plates, cells are grown in Packard flat bottom white polystyrene microplates (Cat No.6005180) in RPMI medium lacking phenol red (AMIMED). Cells are plated at $5 \times 10^4$/well. After treatment of the cells, luciferase is measured using the Packard Luc Lite system (Cat. No.601691 1) according to the manufacturer's instructions in a final volume of 205 μl. Briefly, to a cell suspension of $5 \times 10^5$ cells/ml, γIFN (1000 U/ml Boehringer Mannheim No. 1050494) to a final concentration of 100 U/ml and 0.25% (v/v) Luc Lite Enhancer is added. After a 3 hour incubation LPS (50 μg/ml SIGMA L-8274) is added to give 5 μg/ml final concentration. The cells are then plated at $5 \times 10^4$/100 l/well into flat bottom white polystyrene microplates (Packard, Cat No. 6005180) and incubated for 16 hours. 5 μl of compound solution or control vehicle is then added and the cells are further incubated as indicated. 100 μl of luciferase substrate solution is added and the plates are covered with TopSeal-A press-on adhesive sealing film (Packard Cat.No. 6005185) before measuring luminescence with a Packard Top Count Scintillation Counter at 22° C. The luciferase signal is stable for at least 90 min.

Example 2

Effect of the Radicicol Analog A

The THP-1 cell lines, clone No. 63 (containing PGL2_Neo30) and clone No. 53 (containing pGL2-Control) are grown, differentiated and stimulated with γIFN and LPS identical to normal THP-1 cells. Radicicol analog A is added 16 hours after the addition of LPS and cell extracts are then taken 8 hours later or as indicated. Luciferase activity is inhibited by 1 μM radicicol analog A on average by 50%±17%, in some cases inhibition was as great as 93%, whereas up to $5 \times 10^{-6}$M of radical analog A has no effects on the control clone No. 53, FIG. 3 (solid bars indicate clone No. 53, open bars clone No. 63).

Example 3

Application of Reporter Gene Assay to a Number of Radicicol Analogs

A number of radicicol analogues are tested for their activity in the reporter assay substantially as described in the previous Examples. The results obtained are given in the Table below.

TABLE

| COMPOUND | Luciferase reporter gene assay | | | |
|---|---|---|---|---|
| | clone | 0.5 μM | 1 μM | 5 μM |
| (structure 1) | 53 | 114 | 105 | 107 |
| | 63 | 97 | 88 | 87 |
| (structure 2) | 53 | 68 | 51 | 40 |
| | 63 | 42 | 18 | 3 |
| (structure 3) | 53 | 99 | 77 | 69 |
| | 63 | 88 | 64 | 57 |
| (structure 4) | 53 | 83 | 81 | 70 |
| | 63 | 80 | 66 | 61 |

TABLE-continued

| COMPOUND | Luciferase reporter gene assay | | | |
|---|---|---|---|---|
| | clone | 0.5 μM | 1 μM | 5 μM |
| (structure) | 53 | 103 | 122 | 104 |
| | 63 | 107 | 93 | 70 |
| (structure) | 53 | 136 | 140 | 108 |
| | 63 | 69 | 32 | 9 |
| (structure) | 53 | 97 | 91 | 55 |
| | 63 | 96 | 94 | 7 |

Example 4

Tablets, each comprising e.g. 50 mg of radicicol analog A or a pharmaceutically acceptable salt, are prepared as follows:

| Composition (10000 tablets) | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| Silicon dioxide (highly dispersed) | 20.0 g |
| ethanol | q.s. |

The active ingredient is mixed with the lactose and 292 g of potato starch and the mixture is moistened with an ethanolic solution of the gelatin and granulated through a sieve. After drying, the remainder of the potato starch, the magnesium stearate, the talc and the silicon dioxide are mixed in and the mixture is compressed to form tablets, each weighing 145.0 mg and comprising 50.0 mg of active ingredient; the tablets may, if desired, be provided with breaking notches for finer adaptation of the dose.

Example 5

Film-coated tablet, each comprising 100 mg of radicicol analog A or a pharmaceutically acceptable salt are prepared as follows:

| Composition (for 1000 film-coated tablets) | |
|---|---|
| active ingredient | 100.0 g |
| lactose | 100.0 g |
| corn starch | 70.0 g |
| talc | 60.0 g |
| calcium stearate | 1.5 g |
| hydroxypropylmethylcellulose | 2.36 g |
| shellac | 0.64 g |
| water | q.s |
| methylene chloride | q.s. |

The active ingredient, the lactose and 40 g of the corn starch are mixed and moistened with a paste prepared from 15 g of corn starch and water (with heating) and granulated. The granules are dried, the remainder of the corn starch, the talcum and the calcium stearate are added and mixed with the granules. The mixture is compressed to form tablets (weight: 280 mg) which are then film-coated with a solution of the hydroxypropylmethylcellulose and the shellac in methylene chloride; final weight of the film-coated tablet: 283 mg.

Example 6

Hard gelatin capsules, comprising 100 mg of active ingredient, for example radicicol analog A or a pharmaceutically acceptable salt are prepared, for example, as follows:

| Composition (for 1000 capsules) | |
| --- | --- |
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are intimately mixed. Then first the lactose is added through a sieve of 0.6 mm mesh size and then the microcrystalline cellulose is added through a sieve of 0.9 mm mesh size. The mixture is then intimately mixed again for 10 minutes. Finally the magnesium stearate is added through a sieve of 0.8 mm mesh size. After mixing for a further 3 minutes, size 0 hard gelatin capsules are each filled with 390 mg of the resulting formulation. Soft gelatin capsules may be prepared using similar ingredients and procedures.

What is claimed is:

1. A method for the prophylaxis or treatment of a disease or medical condition having an etiology associated with the increased stability of mRNA which contains one or more mRNA instability sequences, comprising administering to a human or animal patient an effective amount of a compound of Formula II:

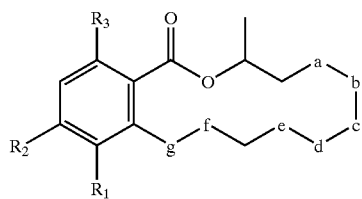

II wherein $R_1$ is H, OH, halogen, $C_1$–$C_4$ lower alkoxy, or $C_1$–$C_4$ lower alkyl-COO—;

$R_2$ is OH, $C_1$–$C_4$ lower alkoxy, or $C_1$–$C_4$ lower alkyl-COO—;

$R_3$ is H, OH, $C_1$–$C_4$ lower alkoxy, or $C_1$–$C_4$ lower alkyl-COO—;

—a—b— is —$CHR_7$—$CHR_8$— or cis or trans —$CR_7$=$CR_8$—;

wherein $R_7$ and $R_8$ are the same or different and are H, OH, $C_1$–$C_4$ lower alkoxy, or $C_1$–$C_4$ lower alkyl-COO—, or —a—b— is —$CHR_7$—$CHR_8$— and $R_7$ and $R_8$ together with O form an epoxide bridge;

c is >CH—OH, >C=O or >$CH_2$;

—d—e— is —$CHR_7$—$CHR_8$— or cis or trans —$CR_7$=$CR_8$—, wherein $R_7$ and $R_8$ are the same or different and are H, OH, $C_1$–$C_4$ lower alkoxy, or $C_1$–$C_4$ lower alkyl-COO—, and —f—g— is —$CH_2$—$CH_2$—, or cis or trans —CH=CH—, or a pharmaceutically acceptable salt thereof or a physiologically-hydrolysable and -acceptable ester thereof, wherein said compound induces degradation of the mRNA, provided that the disease or medical condition is not one with an etiology associated with or comprising excessive cytokine release.

2. A method for inducing degradation of mRNA in a human or animal patient, which comprises administering to said patient an effective amount of a compound of Formula II:

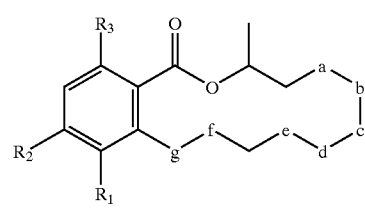

II wherein $R_1$ is H, OH, halogen, $C_1$–$C_4$ lower alkoxy, or $C_1$–$C_4$ lower alkyl-COO—;

$R_2$ is OH, $C_1$–$C_4$ lower alkoxy, or $C_1$–$C_4$ lower alkyl-COO—;

$R_3$ is H, OH, $C_1$–$C_4$ lower alkoxy, or $C_1$–$C_4$ lower alkyl-COO—;

—a—b— is -$CHR_7$—$CHR_8$— or cis or trans —$CR_7$=$CR_8$—;

wherein $R_7$ and $R_8$ are the same or different and are H, OH, $C_1$–$C_4$ lower alkoxy, or $C_1$–$C_4$ lower alkyl-COO—, or —a—b— is —$CHR_7$—$CHR_8$— and $R_7$ and $R_8$ together with O form an epoxide bridge;

c is >CH—OH, >C=O or >$CH_2$;

—d—e— is —$CHR_7$—$CHR_8$— or cis or trans —$CR_7$=$CR_8$—, wherein $R_7$ and $R_8$ are the same or different and are H, OH, $C_1$–$C_4$ lower alkoxy, or $C_1$–$C_4$ lower alkyl-COO—, and —f—g— is —$CH_2$—$CH_2$—, or cis or trans —CH=CH—, or a pharmaceutically acceptable salt thereof or a physiologically-hydrolysable and -acceptable ester thereof, wherein said compound induces mRNA degradation in the patient, and wherein the mRNA contains an mRNA instability sequence, provided that the mRNA is not mRNA coding for IL-1β, IL-6 or TNF-α.

3. A method for the prophylaxis or treatment of a cancer or malignant disease in a human or animal patient comprising administering to the patient an effective amount of a compound of Formula II:

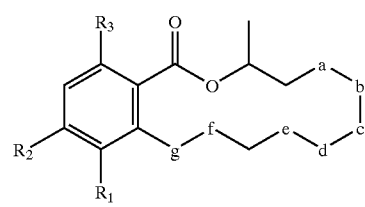

II wherein $R_1$ is OH, halogen, $C_1$–$C_4$ lower alkoxy, or $C_1$–$C_4$ lower alkyl-COO—;

$R_2$ is OH, $C_1$–$C_4$ lower alkoxy, or $C_1$–$C_4$ lower alkyl-COO—;

$R_3$ is H, OH, $C_1$–$C_4$ lower alkoxy, or $C_1$–$C_4$ lower alkyl-COO—;

—a—b— is —CHR$_7$—CHR$_8$— or cis or trans —CR$_7$=CR$_8$—;
  wherein R$_7$ and R$_8$ are the same or different and are H, OH, C$_1$–C$_4$ lower alkoxy, or C$_1$–C$_4$ lower alkyl-COO—, or
—a—b— is —CHR$_7$—CHR$_8$— and R$_7$ and R$_8$ together with O form an epoxide bridge;
c is >CH—OH, >C=O or >CH$_2$;
—d—e— is —CHR$_7$—CHR$_8$— or cis or trans —CR$_7$=CR$_8$—,
  wherein R$_7$ and R$_8$ are the same or different and are H, OH, C$_1$–C$_4$ lower alkoxy, or C$_1$–C$_4$ lower alkyl-COO—, and
—f—g— is —CH$_2$—CH$_2$—, or cis or trans —CH=CH—,
or a pharmaceutically acceptable salt thereof or a physiologically-hydrolysable and -acceptable ester thereof.

4. A method for the treatment or prevention of oncogene mediated cancers or malignant diseases in a human or animal patient comprising administering to the patient an effective amount of a compound of Formula II:

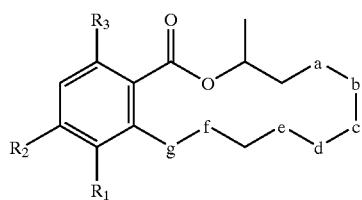

II wherein
  R$^1$ is OH, halogen, C$_1$–C$_4$ lower alkoxy, or C$_1$–C$_4$ lower alkyl-COO—;
  R$_2$ is OH, C$_1$–C$_4$ lower alkoxy, or C$_1$–C$_4$ lower alkyl-COO—;
  R$_3$ is H, OH, C$_1$–C$_4$ lower alkoxy, or C$_1$–C$_4$ lower alkyl-COO—;
  —a—b— is —CHR$_7$—CHR$_8$— or cis or trans —CR$_7$=CR$_8$—;
    wherein R$_7$ and R$_8$ are the same or different and are H, OH, C$_1$–C$_4$ lower alkoxy, or C$_1$–C$_4$ lower alkyl-COO—, or
  —a—b— is —CHR$_7$—CHR$_8$— and R$_7$ and R$_8$ together with O form an epoxide bridge;
  c is >CH—OH, >C=O or >CH$_2$;
  —d—e— is —CHR$_7$—CHR$_8$ — or cis or trans —CR$_7$=CR$_8$—,
    wherein R$_7$ and R$_8$ are the same or different and are H, OH, C$_1$–C$_4$ lower alkoxy, or C$_1$–C$_4$ lower alkyl-COO—, and
  —f—g— is —CH$_2$—CH$_2$—, or cis or trans —CH=CH—,
or a pharmaceutically acceptable salt thereof or a physiologically-hydrolysable and -acceptable ester thereof.

5. A method for the treatment or prevention of tumor growth or metastasis in a human or animal patient comprising administering to the patient an effective amount of a compound of Formula II:

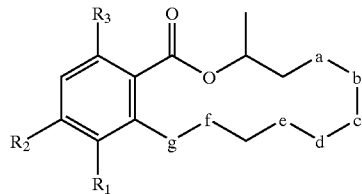

II wherein
  R$_1$ is OH, halogen, C$_1$–C$_4$ lower alkoxy, or C$_1$–C$_4$ lower alkyl-COO—;
  R$_2$ is OH, C$_1$–C$_4$ lower alkoxy, or C$_1$–C$_4$ lower alkyl-COO—;
  R$_3$ is H, OH, C$_1$–C$_4$ lower alkoxy, or C$_1$–C$_4$ lower alkyl-COO—;
  —a—b— is —CHR$_7$—CHR$_8$— or cis or trans —CR$_7$=CR$_8$—;
    wherein R$_7$ and R$_8$ are the same or different and are H, OH, C$_1$–C$_4$ lower alkoxy, or C$_1$–C$_4$ lower alkyl-COO—, or
  —a—b— is —CHR$_7$—CHR$_8$— and R$_7$ and R$_8$ together with O form an epoxide bridge;
  c is >CH—OH, >C=O or >CH$_2$;
  —d—e— is —CHR$_7$—CHR$_8$— or cis or trans —CR$_7$=CR$_8$—,
    wherein R$_7$ and R$_8$ are the same or different and are H, OH, C$_1$–C$_4$ lower alkoxy, or C$_1$–C$_4$ lower alkyl-COO—, and
  —f—g— is —CH$_2$—CH$_2$—, or cis or trans —CH=CH—,
or a pharmaceutically acceptable salt thereof or a physiologically-hydrolysable and -acceptable ester thereof.

6. A method to prevent or reverse multidrug resistance in a tumor cell in a human or animal patient comprising administering to the patient an effective amount of a compound of Formula II:

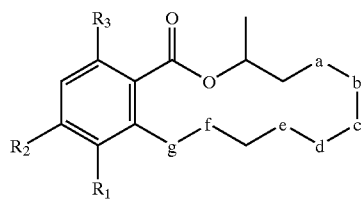

II wherein
  R$_1$ is OH, halogen, C$_1$–C$_4$ lower alkoxy, or C$_1$–C$_4$ lower alkyl-COO—;
  R$_2$ is OH, C$_1$–C$_4$ lower alkoxy, or C$_1$–C$_4$ lower alkyl-COO—;
  R$_3$ is H, OH, C$_1$–C$_4$ lower alkoxy, or C$_1$–C$_4$ lower alkyl-COO—;
  —a—b— is —CHR$_7$—CHR$_8$— or cis or trans —CR$_7$=CR$_8$—;
    wherein R$_7$ and R$_8$ are the same or different and are H, OH, C$_1$–C$_4$ lower alkoxy, or C$_1$–C$_4$ lower alkyl-COO—, or
  —a—b— is —CHR$_7$—CHR$_8$— and R$_7$ and R$_8$ together with O form an epoxide bridge;
  c is >CH—OH, >C=O or >CH$_2$;

—d—e— is —CHR$_7$—CHR$_8$— or cis or trans —CR$_7$=CR$_8$—,
   wherein R$_7$ and R$_8$ are the same or different and are H, OH, C$_1$–C$_4$ lower alkoxy, or C$_1$–C$_4$ lower alkyl-COO—, and
—f—g— is —CH$_2$—CH$_2$—, or cis or trans —CH=CH—, or a pharmaceutically acceptable salt thereof or a physiologically-hydrolysable and -acceptable ester thereof.

7. The method according to claim 3 or 4, wherein said cancer is breast cancer, colon cancer or lung cancer.

* * * * *

UNITED STATES PATENT AND TRADEMARK OFFICE
CERTIFICATE OF CORRECTION

PATENT NO.    : 6,635,671 B1
DATED         : October 21, 2003
INVENTOR(S)   : Kastelic et al.

It is certified that error appears in the above-identified patent and that said Letters Patent is hereby corrected as shown below:

Drawings,
Sheet 1 of 3, please delete the current Figure 1 and insert therein the new Figure 1 that is included herewith.

Column 1,
Line 45, please delete "IFN-Y" and insert therein -- IFN-$\gamma$ --.

Column 7,
Line 67, please delete "zij268" and insert therein -- zif268 --.

Column 8,
Line 21, please delete "(Upa)" and insert therein -- (uPA) --.

Column 9,
Line 29, please delete "mlRNAs" and insert therein -- mRNAs --.
Line 31, please delete "use" and insert therein -- used --.

Column 10,
Lines 6 and 7, please delete "mM" and insert therein -- $\mu$M --.
Line 48, please delete "use" and insert therein -- used --.

Column 11,
Line 20, please insert -- $\mu$g/ml -- following "0.01 to 50".
Line 65, please delete "dragdes" and insert therein -- dragées --.

Column 14,
Line 12, please delete "porter" and insert therein -- reporter --.
Line 42, please delete "7.36 m.M" and insert therein -- 7.36 mM --.
Line 43, please delete "124 mm" and insert therein -- 124 mM --.

UNITED STATES PATENT AND TRADEMARK OFFICE
CERTIFICATE OF CORRECTION

PATENT NO.    : 6,635,671 B1
DATED         : October 21, 2003
INVENTOR(S)   : Katelic et al.

It is certified that error appears in the above-identified patent and that said Letters Patent is hereby corrected as shown below:

Column 15,
Line 2, please delete "as indicated".
Line 16, please delete "/100 1/well" and insert therein -- /100µl/well --.

Signed and Sealed this

Fifth Day of October, 2004

JON W. DUDAS
*Director of the United States Patent and Trademark Office*

```
ATGGCTTCCCTATTTATTTATTTATTTGTTTGTCCAACCT
||||||||||||||||||||||||||||||||||||||||
GGATACCGAAGGGATAAATAAATAAATAAACAAACAGGTT
```

Figure 1